United States Patent
Fix et al.

(10) Patent No.: US 9,664,637 B2
(45) Date of Patent: May 30, 2017

(54) MICROELECTROCHEMICAL SENSOR AND METHOD FOR OPERATING A MICROELECTROCHEMICAL SENSOR

(71) Applicant: Robert Bosch GmbH, Stuttgart (DE)

(72) Inventors: Richard Fix, Gerlingen (DE); Denis Kunz, Untergruppenbach (DE); Andreas Krauss, Tuebingen (DE); Kathy Sahner, Leonberg (DE); Philipp Nolte, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 415 days.

(21) Appl. No.: 14/197,973

(22) Filed: Mar. 5, 2014

(65) Prior Publication Data
US 2014/0262827 A1    Sep. 18, 2014

(30) Foreign Application Priority Data
Mar. 14, 2013   (DE) .................. 10 2013 204 469

(51) Int. Cl.
| | | |
|---|---|---|
| *G01N 27/30* | (2006.01) | |
| *G01N 27/28* | (2006.01) | |
| *G01N 27/406* | (2006.01) | |
| *G01N 27/417* | (2006.01) | |
| *G01N 27/327* | (2006.01) | |

(52) U.S. Cl.
CPC .......... *G01N 27/30* (2013.01); *G01N 27/286* (2013.01); *G01N 27/4065* (2013.01); *G01N 27/417* (2013.01); *G01N 27/3273* (2013.01); *G01N 27/4067* (2013.01)

(58) Field of Classification Search
CPC ............ G01N 27/403; G01N 27/4065; G01N 27/416; G01N 27/286; G01N 27/3273
See application file for complete search history.

(56) References Cited

U.S. PATENT DOCUMENTS

| | | | | |
|---|---|---|---|---|
| 5,498,487 A | * | 3/1996 | Ruka .................. | G01N 27/4067 429/425 |
| 2001/0037949 A1 | * | 11/2001 | Patko .................. | G01N 27/333 205/775 |
| 2006/0069871 A1 | * | 3/2006 | Gill ...................... | G06F 12/0862 711/118 |
| 2006/0096871 A1 | * | 5/2006 | Manoukian ........ | G01N 27/4074 205/782 |
| 2008/0299427 A1 | * | 12/2008 | Tanaka .............. | H01M 8/04014 429/436 |

FOREIGN PATENT DOCUMENTS

DE          199 41 051 A1     3/2001

* cited by examiner

*Primary Examiner* — Alexander Noguerola
(74) *Attorney, Agent, or Firm* — Maginot, Moore & Beck LLP

(57) ABSTRACT

A microelectrochemical sensor includes an energy supply unit and a sensor unit. The energy supply unit is configured to generate electrical energy using a reference fluid. The sensor unit is configured to determine a concentration difference of a chemical species between a measuring fluid and the reference fluid. The measuring fluid has an unknown concentration of the species, and the reference fluid has a known concentration of the species. The sensor unit is electrically connected to the energy supply unit and is designed to determine the concentration difference using the electrical energy from the energy supply unit.

12 Claims, 3 Drawing Sheets

MICROELECTROCHEMICAL SENSOR AND METHOD FOR OPERATING A MICROELECTROCHEMICAL SENSOR

This application claims priority under 35 U.S.C. §119 to patent application no. DE 10 2013 204 469.0, filed on Mar. 14, 2013 in Germany, the disclosure of which is incorporated herein by reference in its entirety.

BACKGROUND

The present disclosure relates to a microelectrochemical sensor, to a method for operating a microelectrochemical sensor and to a corresponding computer program product.

In order to be able to adapt a ratio between a quantity of fuel for a combustion process and an available quantity of oxygen, definitive information is required about an oxygen concentration in an exhaust gas of the combustion process. Since the exhaust gas usually is at a high temperature at a measuring point, a temperature-resistant sensor is required to determine the oxygen concentration.

DE 199 41 051 A1 describes a sensor element for determining the oxygen concentration in gas mixtures, and a method for producing same.

SUMMARY

Against this background, the present disclosure presents a microelectrochemical sensor, method for operating a microelectrochemical sensor and finally a corresponding computer program product according to the disclosure. Advantageous refinements can be found in the claims and the following description.

A sensor requires electrical energy for operation. In a vehicle, the electrical energy can be made available via an on-board power system. However, as a result an at least two-conductor energy supply line is necessary per sensor. In addition, an at least single-conductor data line is necessary. These multiple cables are connected to form a cable harness which can reach a large overall length. Through multiple use of lines it is possible to reduce the number of cables. By means of bus systems, a plurality of sensors and/or vehicle components can be connected via a bus line.

The sensor may just be connected to a data line, in particular to a bus line, if the sensor has a separate energy source which is sufficiently dimensioned to supply the sensor. Owing to the progressive miniaturization in processing engineering, ever smaller energy consumption levels can be achieved, since sensor elements require an ever smaller area to make available a signal. The necessary energy supply capacity of an energy source drops to the same extent as the reduction in the required areas and layer thicknesses.

A microelectrochemical sensor having the following features is presented:

an energy supply unit for generating electrical energy using a reference fluid; and a sensor unit for determining a concentration difference of a chemical species between a measuring fluid with an unknown concentration of the species and the reference fluid which has a known concentration of the species, wherein the sensor unit is electrically connected to the energy supply unit and is designed to determine the concentration difference using the electrical energy from the energy supply unit.

Furthermore, a method for operating a microelectrochemical sensor according to the approach presented here is presented, wherein the method has the following steps:

generating electrical energy using a reference fluid and determining a concentration difference of a chemical species between a measuring fluid with an unknown concentration of the species and the reference fluid with a known concentration of the species using the electrical energy.

A microelectrochemical sensor can be understood to be a miniaturized sensor for sensing and imaging a physical variable in a signal. The signal can be made available via a data line. A chemical species can be a chemical element, a molecule or a chemical compound. The signal can be an electrical signal. An energy supply unit can be a power source and/or voltage source which is designed to use an energy potential of at least one medium in order to acquire electrical energy for the sensor. For example, the energy supply unit can use a chemical energy potential while synthesizing the medium with at least one further medium to form a new medium in order to acquire electrical energy. The energy supply unit can also use a thermal energy potential between two media or between the medium in a first state and the medium in a second state in order to acquire electrical energy. The medium can be contained in the reference fluid. The chemical species can be the medium. The electrical energy can be used, for example, to adjust the temperature of the sensor to an operating temperature. The electrical energy can also be used to process the signal. For example, the signal can be amplified.

The method can have a step of making available a concentration signal, wherein the concentration signal represents the concentration difference, and the concentration signal is determined using the electrical energy. A concentration signal can be a digital signal. For example, the concentration difference can be represented in a sequence of pulses. Likewise, the concentration difference can be transmitted in a multiplicity of signal states in parallel over a plurality of lines. The digitization can take place using the electrical energy.

The energy supply unit can be designed to make available the electrical energy also using an energy fluid as an energy carrier. The energy potential can be present between the reference fluid and the energy fluid. The energy fluid can be the same fluid as the measuring fluid. For example, the energy fluid can have thermal energy which can be converted into electrical energy via a thermoelectric element. The energy fluid can then be hot exhaust gas which outputs a heat flow to the thermoelectric element, wherein the heat flow flows through the thermoelectric element and generates electrical energy. The heat flow can then be output to the reference fluid by the thermoelectric element. The energy fluid can also be a chemical energy carrier.

The energy supply unit can have a diaphragm which fluidically separates a reference duct for the reference fluid from a supply duct for the energy fluid. The electrical energy can be tappable at the diaphragm if the reference fluid and the energy fluid are present at the diaphragm. A reference duct can be designed to conduct the reference fluid. A supply duct can be designed to conduct the energy fluid. The reference duct and the supply duct can conduct the reference fluid and the energy fluid fluidically separated from one another. A diaphragm can be a thin dividing wall between the ducts.

The energy fluid can be a proton donor. The energy supply unit can be designed to make available the electrical energy catalytically. The energy fluid can have chemical energy which can be converted into electrical energy by means of a catalytic element. The energy fluid can be stored in an accumulator or tank and used when necessary. A proton donor can be a hydrogen cation donor. The proton donor can be a chemical compound which splits hydrogen atoms and/or hydrogen ions as soon as activation energy is made available for splitting. The activation energy may be less than energy which is released when recombination of the hydrogen atoms occurs.

For example, the proton donor can be a hydrocarbon compound or pure hydrogen. A catalyst can reduce the activation energy for splitting the hydrogen. The electrical energy can be acquired by synthesis of the hydrogen with oxygen from the reference fluid to produce water. The diaphragm can be permeable to oxygen ions and/or hydrogen ions. The electrical energy can be tapped at electrodes on the diaphragm.

The sensor unit can have a tank for storing the energy fluid, wherein the tank is connected to the supply duct of the energy supply unit. The tank can be a pressure-resistant container which can store, for example, a compressed combustion gas. The tank can have a valve which is controlled using the electrical energy acquired in the energy supply unit. A pressure in the supply duct can be regulated by means of the valve. The tank can be exchangeable. The tank can be refillable. The tank can be designed to store a liquid. For this purpose, the tank can have a metering device, for example a pump, which can convey the liquid into the supply duct in a metered fashion.

The sensor unit can have a sensor diaphragm which fluidically separates a reference duct for the reference fluid from a measuring duct for the measuring fluid. The sensor diaphragm can have a first electrode in the reference duct and a second electrode in the measuring duct. An electrical voltage potential can be tappable between the first electrode and the second electrode if the concentration difference between the reference fluid and the measuring fluid is present. The sensor diaphragm can be permeable to ions of the chemical species. The chemical species can be ionized on both surfaces of the sensor diaphragm, for example by means of heat and/or a catalyst. During ionization, at least one electron is separated from an ion. The electrons can move in the electrodes. A quantity of the ions on one side is in equilibrium with the concentration or a partial pressure of the species in the respectively present fluid. In the case of the concentration difference is present between the reference fluid and the measuring fluid, more ions are produced on one side of the sensor diaphragm than on the other side. This difference is compensated by migration of the ions from the high concentration to the low concentration. The separated electrons cannot follow the migration, which gives rise to a voltage potential between the electrodes. A level of the voltage is correlated to the concentration difference here.

The sensor unit can be designed to determine the concentration difference between a combustion exhaust gas as the measuring fluid and ambient air as the reference fluid. In particular, the sensor unit can be designed to detect the concentration difference of oxygen between the combustion exhaust gas and the ambient air. The combustion exhaust gas can be hot. The combustion exhaust gas can heat the sensor unit and/or the energy supply unit, with the result that only a small quantity of electrical energy is then required to adjust the temperature of the sensor unit.

The microelectrochemical sensor can have a base body in which the energy supply unit is arranged next to the sensor part. The base body can have conductor tracks which connect the energy supply unit electrically to the sensor unit.

The microelectronic sensor can be arranged on a contiguous chip. The sensor can be arranged on a semiconductor substrate. The sensor can be manufactured using semiconductor technology.

The diaphragm of the energy supply unit can be of the similar design to the sensor diaphragm of the sensor part. The diaphragm can be permeable to the ions of the same chemical species. The diaphragm can have the same material. The diaphragm can be equipped with the same catalyst. The sensor unit and the energy supply unit can be manufactured cost-effectively and quickly through diaphragm structures of the same type.

The microelectrochemical sensor can have an electronic unit which is designed to actuate the energy supply unit and the sensor unit using the electrical energy, and to make available a concentration signal which represents the concentration difference. The electronic unit can have integrated circuits. For example, the electronic unit can be arranged in the semiconductor substrate of the base body. The electronic unit can, for example, be designed to regulate a voltage for operating the sensor unit.

A computer program product having program code which can be stored on a machine-readable carrier such as a semiconductor memory, a hard disk memory or an optical memory, and is used to carry out the method according to one of the embodiments described above is also advantageous if the program product is executed on a computer or a device.

BRIEF DESCRIPTION OF THE DRAWINGS

The disclosure will be explained in more detail below by way of example with reference to the appended drawings, of which.

DETAILED DESCRIPTION

In the following description of preferred exemplary embodiments of the present disclosure, identical or similar reference symbols are used for the similarly acting elements which are illustrated in the various figures, wherein a repeated description of these elements is dispensed with.

Figure 1:
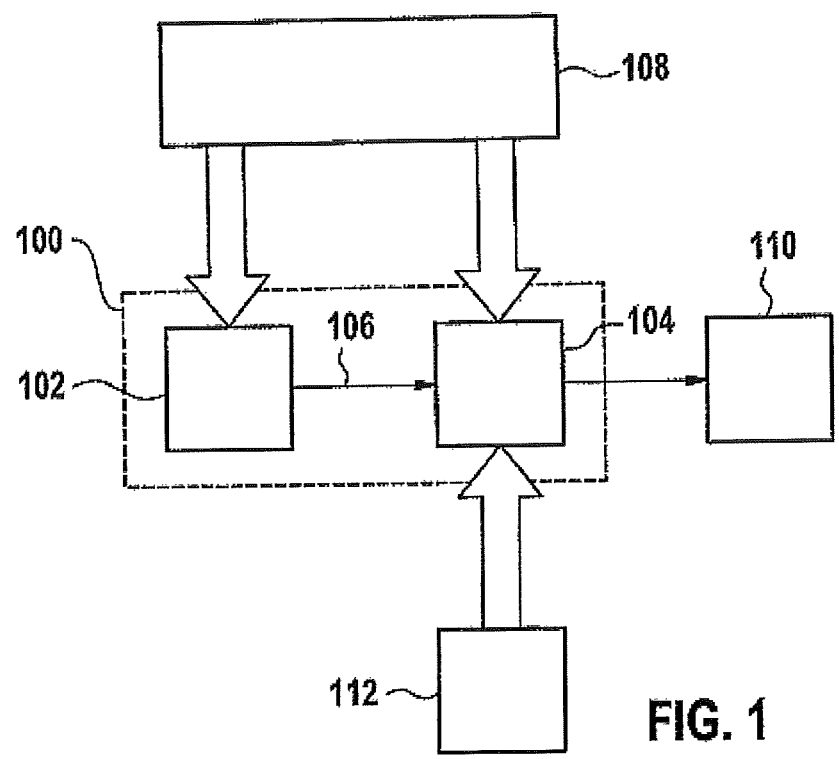
FIG. 1 shows a block circuit diagram of a microelectrochemical sensor according to an exemplary embodiment of the present disclosure.

FIG. 1 shows a block circuit diagram of a microelectrochemical sensor 100 according to an exemplary embodiment of the present disclosure. The sensor 100 has an energy supply unit 102 which forms, in particular, an autonomous energy supply unit, and a sensor unit 104. The energy supply unit 102 is designed to generate electrical energy 106 using a reference fluid 108. The sensor unit 104 is designed to determine a concentration difference 110 of a chemical species between a measuring fluid 112 with an unknown concentration of the species and the reference fluid 108 which has a known concentration of the species. The sensor unit 104 is electrically connected to the energy supply unit 102. The sensor unit 104 is designed to determine the concentration difference 110 using the electrical energy 106 from the energy supply unit 102.

Figure 2:
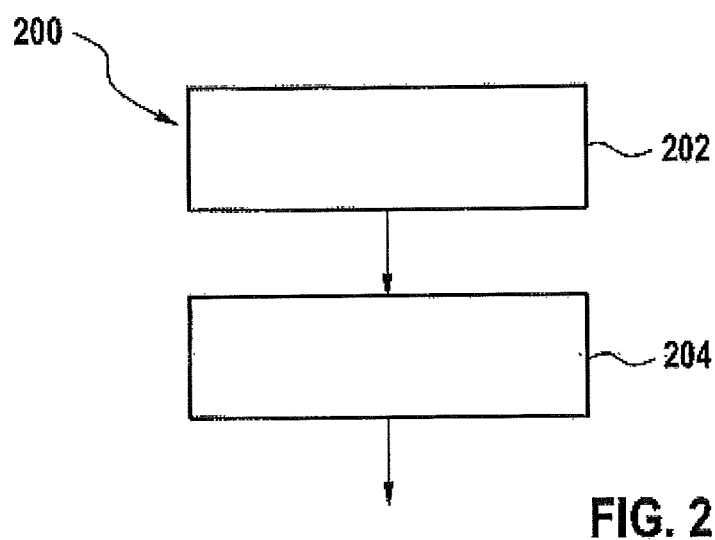
FIG. 2 shows a flowchart of a method for operating a microelectrochemical sensor according to an exemplary embodiment of the present disclosure.

FIG. 2 shows a flowchart of a method 200 for operating a microelectrochemical sensor according to an exemplary embodiment of the present disclosure. For example, the microelectrochemical sensor is illustrated in FIG. 1. The method 200 has a generating step 202 and a determining step 204. In the generating step 202, electrical energy is generated using a reference fluid. In the determining step 204, a concentration difference of a chemical species between a measuring fluid with an unknown concentration of the species and the reference fluid with a known concentration of the species is determined using the electrical energy.

Figure 3:
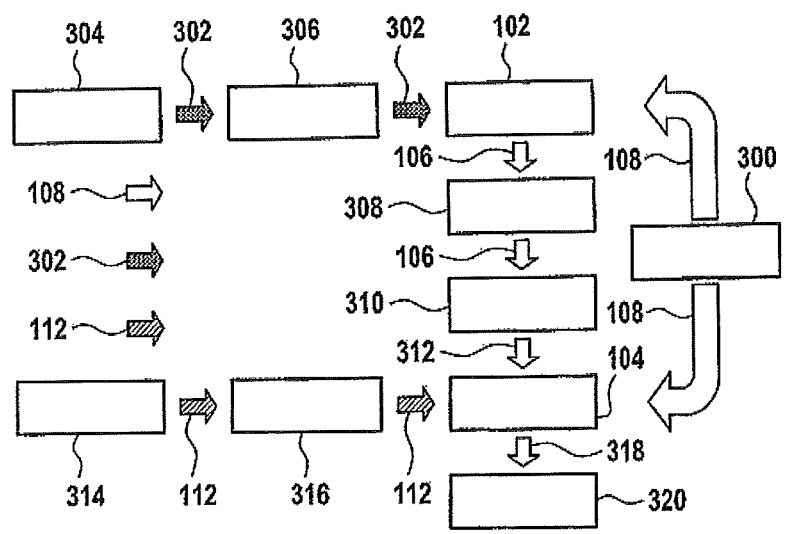
FIG. 3 shows a block illustration of a microelectrochemical sensor with peripherals according to an exemplary embodiment of the present disclosure.

FIG. 3 shows a block illustration of a microelectrochemical sensor with peripherals according to an exemplary embodiment of the present disclosure. The sensor has, as in FIG. 1, an energy supply unit 102 and a sensor unit 104. The energy supply unit 102 is embodied as a miniaturized solid oxide fuel cell (μSOFC). The sensor unit 104 is embodied as a sensor cell. Both the sensor unit 104 and the energy supply unit 102 are supplied with air 108 as a reference fluid. The air 108 is fed to the sensor unit 104 and to the energy supply unit 102 via an air feed line 300. The energy supply unit 102 is also supplied here with a combustion gas 302. The combustion gas 302 is stored in a tank 304. The combustion gas 302 is conducted from the tank 304 through first microfluidics 306 to the solid oxide fuel cell 102. In the solid oxide fuel cell 102, oxygen molecules are ionized from the air 108 and combined catalytically with hydrogen cations or hydrogen ions from the combustion gas 302 to form water vapor. In this context, electrical energy 106 in the form of electrical current $I_{electrical}$ and electrical voltage are produced in the solid oxide fuel cell 102. The electrical energy 106 is adapted to an energy requirement of the sensor unit 104 in electronics 308. The energy requirement is mainly determined by a miniaturized heater 310 of the sensor unit 104. The heater 310 makes available heat 312 in order to adjust the sensor unit to an operating temperature. The sensor unit 104 is supplied here with measuring gas 112 as the measuring fluid. The measuring gas 112 is conducted from a measuring space 314 through second microfluidics 316 to the sensor cell 104. Oxygen molecules from the air 108 are also ionized in the sensor unit 104 which is heated to operating temperature. In contrast to the solid oxide fuel cell 102, oxygen molecules are, however, also ionized from the measuring gas 112. A quantity of the ions is in equilibrium here with a concentration of the oxygen in the respective gas 108, 112. During the ionization, electrons are split off. The electrons on the air side form a first voltage level. The electrons on the measuring gas side form a second voltage level. A voltage potential 318 between the first voltage level and the second voltage level represents a ratio of the oxygen concentrations in the air 108 and the measuring gas 112. The voltage potential 318 makes available an electrical signal at a signal output 320 of the sensor.

The high temperature fuel cell 102 (SOFC, solid oxide fuel cell) can be embodied in a miniaturized form. In this context, ceramic materials from conventional SOFC technology are combined with microfabrication steps from semiconductor processing technology in order to form a micro SOFC 102. Such miniaturized energy converters 102 form a possible alternative for conventional accumulators (in particular Li ion accumulators) as a power supply for electronic devices. The main advantage over traditional energy accumulators is the rapid "rechargeability". While batteries have to be connected to a stationary power supply over a relatively long time period for charging, in the case of the fuel cell solution a separate tank is refilled with fuel. A tank concept which can be provided is, for example, a liquid gas cartridge such as, for example, in a lighter.

Ceramic exhaust gas sensors 104 can also be miniaturized in parallel. The reduction in size of the sensor elements 104 is attractive owing to the saving in material which can be achieved in the case of costly materials, and the low heating power demand which is required. Operating temperatures above 400° C. are typically necessary to ensure the sensor function. The necessary heating power has been made available hitherto by a separate energy carrier (for example the on-board power system in the motor vehicle). An exemplary embodiment described here is the lambda probe 104. With the approach presented here, further ceramic gas sensors, for example $NO_x$ sensors for nitrogen oxides, HC sensors for hydrocarbons, $NH_3$ sensors for ammonia can be operated autonomously.

Figure 4:
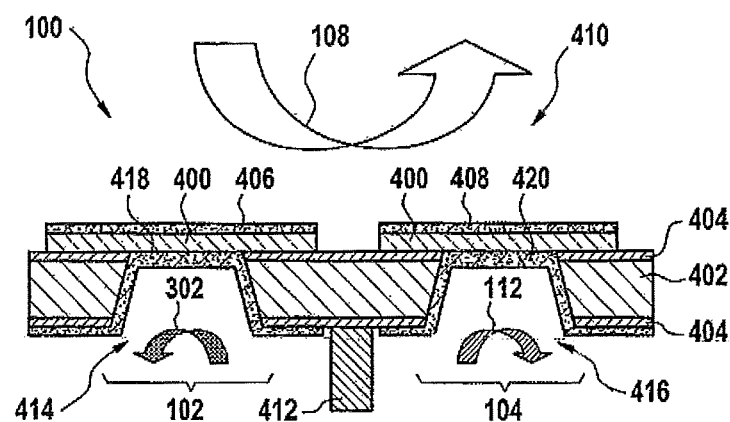
FIG. 4 shows an illustration of a microelectrochemical sensor with diaphragms of the same design, according to an exemplary embodiment of the present disclosure.

FIG. 4 shows an illustration of a microelectrochemical sensor 100 with diaphragms 400 of the same design according to an exemplary embodiment of the present disclosure. The sensor corresponds to the sensor in FIG. 3. In addition, the energy supply unit 102 in the form of a micro-solid oxide fuel cell and the sensor unit 104 are integrated into a common semiconductor substrate 402. The semiconductor substrate 402 serves here as a microstructured carrier of the sensor. The semiconductor substrate 402 has passivation 404 on both sides. A first diaphragm 400 of the energy supply unit 102 and a second diaphragm 400 of the sensor unit 104 are arranged on a first side of the semiconductor substrate 402. The diaphragms 400 are embodied here as oxygen ion-conducting ceramic made of yttrium-stabilized zirconium oxide (YSZ). A first electrode 406 is arranged on the first diaphragm 400. A second electrode 408 is arranged on the second diaphragm 400. The electrodes 406, 408 are arranged in a reference duct 410. The first electrode 406 and the second electrode 408 are embodied as air electrodes here and have platinum as a catalyst. The air electrodes 406, 408 can be supplied with air 108. A fluidtight dividing wall 412 is arranged on a second side of the semiconductor substrate 402 lying opposite the first side. The dividing wall 412 separates a supply duct 414 for the combustion gas 302 from a measuring duct 416 for the measuring gas 112. A third electrode 418 is arranged on the second side of the semiconductor substrate 402 in the region of the supply duct 414. The third electrode 418 extends over the semiconductor substrate 402 of the supply duct 414, lines a first cutout in the semiconductor substrate 402 and extends over the first diaphragm 400. The third electrode 418 is embodied as a combustion gas electrode and has platinum. A fourth electrode 420 is arranged in the region of the measuring duct 416, on the second side of the semiconductor substrate 402. The fourth electrode 420 extends over the semiconductor substrate 402 of the measuring duct 416, lines a second cutout in the semiconductor substrate 402 and extends over the second diaphragm 400. The fourth electrode 420 is embodied as a measuring electrode and also has platinum.

In other words, FIG. 4 shows a sectional illustration through a lambda probe 100 which is independent of the on-board power system. In particular, the lambda probe 104 is technologically very close to the SOFC 102. The basic material for both applications is an oxygen ion-conducting ceramic 400 which can be embodied as yttrium-stabilized zirconium oxide, YSZ. For example Pt (platinum) is possible as the electrode material. The approach presented here shows a combination of the elements SOFC 102 and MECS 104 (MECS=microelectrochemical sensor).

The lambda probe 104 can be miniaturized using the semiconductor processing technology. Since both microconcepts 102, 104 are very similar in materials, structures and processes used, both elements can be integrated on a chip 402. As a result, a sensor subsystem 100 can be formed which is not dependent on the on-board power system or similar energy sources. By integrating a miniaturized SOFC 102 and a miniaturized lambda probe 104 on a chip 402 it is possible to form a sensor subsystem 100 which connects a power source 102 and a load 104 in a space-saving fashion and operates independently of batteries or the on-board power system.

Figure 5:
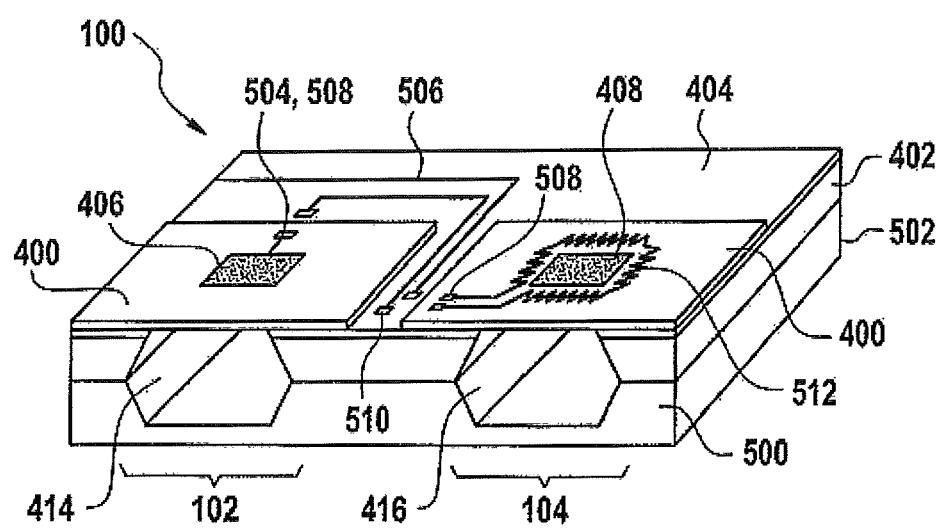
FIG. 5 shows a spatial illustration of an autonomous microelectrochemical sensor in a common base body according to an exemplary embodiment of the present disclosure.

FIG. 5 shows a spatial illustration of a microelectrochemical sensor 100 in a common base body 500 according to an exemplary embodiment of the present disclosure. The sensor 100 corresponds to the sensor in FIG. 4. A further chip 502 to form the base body is additionally added to the semiconductor substrate 402. The further chip 502 closes off a side of the supply duct 414 and of the measuring duct 416 facing away from the diaphragms 400. As a result, the supply duct 414 and the measuring duct 416 run within the base body 500 and form the first microfluidic system and the second microfluidic system. The first diaphragm 400 of the energy supply unit 102 and the second diaphragm 400 are of rectangular shape. The first diaphragm 400 and the second diaphragm each extend over only a partial region of the carrier material 402. The passivation 404 is exposed outside the diaphragms 400. In contrast to FIG. 4, the first electrode 406 and the second electrode 408 extend only over a central region of the respective diaphragm 400. Contact is made with the electrodes 406, 408 via conductor tracks 504 on the diaphragms 400. In order to be placed in electrical contact with conductor tracks 506 on the base body 500, the conductor tracks 504 each have a bond pad 508 at the end. The conductor tracks 506 also have bond pads 510. Associated bond pads 508, 510 are connected in an electrically conductive fashion via a bond wire. The conductor tracks 506 of the base body 500 are connected to an electronic unit which is integrated into the carrier material 402. The electronic unit regulates the electrical energy from the fuel cell 102 in order to actuate the sensor 104. The sensor 102 has a microheater 512 which runs around the second electrode 408 and which is embodied as a meandering resistance conductor track on the second diaphragm. The microheater 512 is also connected to the electronic unit via conductor tracks 504 and bond pads 508 and is supplied with electrical energy by the electronic unit.

The system 100 outlined in FIGS. 4 and 5 is based on a semiconductor chip 402, 500, 502, for example composed of SiC or Si with suitable passivation layers 404 in which ducts 414, 416 and hollow chambers 414, 416 for microfluidics are processed using semiconductor processing technology. The chip 500 has at least two areas with ceramic YSZ diaphragms 400 which are coated with suitable electrode materials (for example Pt) on both sides. One of the regions 400 performs the function of a micro-SOFC 102, and the second the function of a ceramic gas sensor 104 (for example of a lambda probe).

Basically, expansion into a plurality of SOFC units 102 and/or a plurality of sensor cells 104 on one chip 500 is possible.

An electrode 418 of the SOFC cell 102 is connected via a suitable microfluidic system 414 to a separate, easily exchangeable or suitably dimensioned fuel tank (for example a liquid gas cartridge). An electrode 420 of the gas sensor cell 104 is in contact via a duct system 416 with the gas 112 to be measured. The respective second electrode 406, 408 of both the SOFC 102 and the sensor element 104 is in contact with an oxygen-containing gas 108, in the simplest case air. The encapsulation of the chip 500 is embodied in such a way that the supply of fresh air 108 to these electrodes 406, 408 is always sufficiently possible.

The SOFC unit 102 is connected to a microstructured heater 512 for the sensor cell 104 via microstructured conductor tracks 506. In addition, electronics for resistance temperature control of the sensor cell 104 can be accommodated on the chip 500.

The chemical energy of the fuel 302 is converted into electrical energy in the fuel cell 102. The resulting electrical current is fed to the heater 512 via the conductor tracks 506 and brings about heating of the sensor cell 104 there in order to make the latter operationally ready.

The described exemplary embodiments which are shown in the figures are selected only by way of example. Different exemplary embodiments can be combined with one another completely or with respect to individual features. An exemplary embodiment can also have features of a further exemplary embodiment added to it.

In addition, method steps according to the disclosure can be repeated and implemented in another sequence to that described.

If an exemplary embodiment comprises an "and/or" conjunction between a first feature and a second feature, this is to be understood as meaning that the exemplary embodiment according to one embodiment has both the first feature and the second feature, and according to a further embodiment has either only the first feature or only the second feature.

What is claimed is:

1. A microelectrochemical sensor comprising:
   an energy supply unit configured to generate electrical energy using a reference fluid with a known concentration of a chemical species; and
   a sensor unit configured to determine a concentration difference of the chemical species between a measuring fluid with an unknown concentration of the species and the reference fluid,
   wherein the sensor unit:
   is electrically connected to the energy supply unit; and
   is configured to determine the concentration difference using the electrical energy.

2. The microelectrochemical sensor according to claim 1, wherein the energy supply unit is further configured to generate the electrical energy using an energy fluid as an energy carrier.

3. The microelectrochemical sensor according to claim 2, wherein:
   the energy supply unit includes a diaphragm that fluidically separates the a reference duct for the reference fluid from a supply duct for the energy fluid; and
   the electrical energy is tappable at the diaphragm when the reference fluid and the energy fluid are present at the diaphragm.

4. The microelectrochemical sensor according to claim 3, wherein the energy fluid is a proton donor and the energy supply unit is configured to catalytically generate the electrical energy.

5. The microelectrochemical sensor according to claim 3, wherein:
   the sensor unit comprises a sensor diaphragm that fluidically separates a reference duct for the reference fluid from a measuring duct for the measuring fluid;

the sensor diaphragm includes:
a first electrode in the reference duct; and
a second electrode in the measuring duct;
an electrical voltage is tappable between the first electrode and the second electrode when the concentration difference between the reference fluid and the measuring fluid is present; and
the diaphragm of the energy supply unit is of a substantially identical configuration as the sensor diaphragm.

6. The microelectrochemical sensor according to claim 1, wherein:
the sensor unit comprises a sensor diaphragm that fluidically separates a reference duct for the reference fluid from a measuring duct for the measuring fluid;
the sensor diaphragm includes:
a first electrode in the reference duct; and
a second electrode in the measuring duct; and
an electrical voltage is tappable between the first electrode and the second electrode when the concentration difference between the reference fluid and the measuring fluid is present.

7. The microelectrochemical sensor according to claim 1, wherein:
the measuring fluid is a combustion exhaust gas; and
ambient air is the reference fluid.

8. The microelectrochemical sensor according to claim 1, wherein:
a base body comprises the energy supply unit and the sensor unit;
the energy supply unit is positioned next to the sensor unit; and
the base body further comprises conductor tracks that electrically connect the energy supply unit to the sensor unit.

9. The microelectrochemical sensor according to claim 1, further comprising an electronic unit configured to:
actuate the energy supply unit and the sensor unit using the electrical energy; and
generate a concentration signal representative of the concentration difference.

10. A method of using a microelectrochemical sensor, comprising:
using an energy supply unit of the microelectrochemical sensor to generate electrical energy using a reference fluid with a known concentration of a chemical species; and
using a sensor unit of the microelectrochemical sensor to determine a concentration difference of the chemical species between a measuring fluid with an unknown concentration of the species and the reference fluid using the electrical energy,
wherein the sensor unit is electrically connected to the energy supply unit.

11. The method of using the microelectrochemical sensor according to claim 10, further comprising generating a concentration signal representative of the concentration difference, wherein the concentration signal is determined using the electrical energy.

12. A non-transitory computer-readable data storage device comprising program code that, when executed by a processor of a computing device, causes the computing device to:
using an energy supply unit of the microelectrochemical sensor to generate generating electrical energy using a reference fluid with a known concentration of a chemical species; and
using a sensor unit of the microelectrochemical sensor to determine determining a concentration difference of the chemical species between a measuring fluid with an unknown concentration of the species and the reference fluid using the electrical energy,
wherein the sensor unit is electrically connected to the energy supply unit.

* * * * *